United States Patent
Shirahata et al.

(10) Patent No.: US 6,500,458 B1
(45) Date of Patent: Dec. 31, 2002

(54) CONDENSATE OF SAR ABOLISHER, PRODUCING METHOD THEREOF, AND SAR ABOLISHER POWDER

(75) Inventors: Sanetaka Shirahata, Fukuoka (JP); Kazumichi Otsubo, Osaka (JP)

(73) Assignee: Shinkatsu Morisawa, Osaka (JP)

( * ) Notice: Subject to any disclaimer, the term of this patent is extended or adjusted under 35 U.S.C. 154(b) by 0 days.

(21) Appl. No.: 09/714,113

(22) Filed: Nov. 17, 2000

(30) Foreign Application Priority Data

Nov. 19, 1999 (JP) .......................... 11-329231

(51) Int. Cl.[7] .......................... A61K 9/16; A01N 43/78
(52) U.S. Cl. ........................ 424/466; 504/266
(58) Field of Search .......................... 424/466; 504/266

(56) References Cited

U.S. PATENT DOCUMENTS 5,378,339 A  1/1995  Aoki et al.

FOREIGN PATENT DOCUMENTS

| EP | 0531783 A1 | 3/1993 |
| EP | 0752391 A2 | 1/1997 |
| EP | 0752391 | * 8/1997 |
| EP | 0 826 636 A1 | 3/1998 |
| EP | 11192485 | * 7/1999 |
| EP | 0987222 A2 | 3/2000 |
| JP | 10-118653 | 5/1998 |
| JP | 11-192485 | 7/1999 |

OTHER PUBLICATIONS

Shirahata et al. "Electrolyzed–Reduced water scavenges active oxygen species and protects DNA from oxidative damage", Biochemcial and Biophysical Research Communications, 234 (269–274), 1997.*

Shirahata, S., et al., *"Electrolyzed–Reduced Water Scavanges Active Oxygen Species and Protects DNA from Oxidative Damage"*, Biochemical and Biophysical Research Communications, Academic Press Inc., vol. 234, No. 1, 1997, pp. 269–274, XP000978700.

European Search Report.

* cited by examiner

Primary Examiner—Jose' G. Dees
Assistant Examiner—R. DeWitty
(74) Attorney, Agent, or Firm—McDermott, Will & Emery

(57) ABSTRACT

Condensate of superoxide anion radical (SAR) abolisher exhibiting strong and stable SAR abolishing activity is provided. Hydrogen adsorbent is introduced into a solution obtained by dissolving electrolyte into purified water. The solution containing hydrogen adsorbent is introduced into both cathode and anode chambers separated by a diaphragm. With a cathode immersed in the cathode chamber and with an anode immersed in the anode chamber, electricity is applied between the cathode and the anode to electrolyze the solution. Electrolytic reduced water produced in the cathode chamber is derived, and water included in the electrolytic reduced water is evaporated.

9 Claims, 4 Drawing Sheets

30: CARTRIDGE CONTAINING ACTIVATED CARBON

CONDENSATE OF SAR ABOLISHER, PRODUCING METHOD THEREOF, AND SAR ABOLISHER POWDER

BACKGROUND OF THE INVENTION

1. Field of the Invention

The present invention generally relates to condensate of superoxide anion radical (SAR) abolisher, and more particularly, to condensate of SAR abolisher that has potency to abolish SAR that causes diseases such as cerebral stroke, cardiac infarction, arteriosclerosis, cancer and the like. The present invention also relates to a method of producing such condensate of SAR abolisher. The present invention further relates to SAR abolisher powder having potency to abolish SAR.

2. Description of the Background Art

In recent years, mortality from cancer has been rising all over the world. A major factor of the death by cancer is remote metastasis to other organs, which in many cases has already occurred when a person is given a diagnosis of cancer.

In the current cancer treatment, however, cure is often difficult once the cancer has metastasized. Solving this problem will be a key to overcome the cancer. The cancer is considered to occur due to damage to DNA that is caused by SAR. The applicant has already proposed high concentration hydrogen dissolved water obtained by electrolysis, which has potency to prevent or repair such damage to the DNA caused by SAR (Japanese Patent Laying-Open No. 10-118653).

To evaluate SAR abolishing capability of reduced water obtained by electrolysis (hereinafter, referred to as "electrolytic reduced water"), a solution of super purified water with 0.01% NaCl added therein was first electrolyzed by an electrolysis apparatus ("TI-8000"). The SAR abolishing capability of the electrolytic reduced water thus obtained was evaluated by a chemiluminescence analyzer using luminol luminescent reagent as reactant. The result showed that the reaction was weak, and the SAR abolishing activity was small.

SUMMARY OF THE INVENTION

Based on the above, a main object of the present invention is to provide condensate of SAR abolisher improved to exhibit strong and stable SAR abolishing activity.

Another object of the present invention is to provide a method of producing such condensate of SAR abolisher.

A further object of the present invention is to provide SAR abolisher powder exhibiting strong SAR abolishing activity.

In the method of producing condensate of SAR abolisher according to a first aspect of the present invention, hydrogen adsorbent is first introduced into a solution obtained by dissolving electrolyte into purified water. The solution containing the hydrogen adsorbent is then introduced into both a cathode chamber and an anode chamber separated from each other by a diaphragm. With a cathode immersed in the cathode chamber and an anode immersed in the anode chamber, electricity is applied between the cathode and the anode to electrolyze the solution. Electrolytic reduced water is obtained in the cathode chamber, which is derived therefrom. Water contained in the electrolytic reduced water is then evaporated.

In the method of producing condensate of SAR abolisher according to a second aspect, the hydrogen adsorbent to be used may be selected from carbon (C), platinum (Pt), platinum salt ($H_2PtCl_6$), gold (Au), vanadium (V) and palladium (Pd), which are substances capable of adsorbing hydrogen (H., $H_2$).

In the method of producing condensate of SAR abolisher according to a third aspect, the electrolyte includes NaCl or NaOH.

In the method of producing condensate of SAR abolisher according to a fourth aspect, the step of introducing the hydrogen adsorbent into a solution obtained by dissolving electrolyte into purified water includes the step of causing the solution containing the electrolyte to pass through a cartridge including the hydrogen adsorbent.

In the method of producing condensate of SAR abolisher according to a fifth aspect, a solution obtained by dissolving electrolyte into purified water is first introduced into both a cathode chamber and an anode chamber separated from each other by a diaphragm. A first cathode for electrolysis is immersed in the cathode chamber, and a first anode for the electrolysis is immersed in the anode chamber. A second cathode is also immersed in the cathode chamber, and a second anode, formed of hydrogen adsorbent, is immersed in the anode chamber for application of electricity between itself and the second cathode. Electricity is applied between the first cathode and the first anode to electrolyze the solution. Electricity is also applied between the second cathode and the second anode to dissolve the hydrogen adsorbent into the solution. Electrolytic reduced water produced in the cathode chamber is derived. Water within the electrolytic reduced water is then evaporated.

In the method of producing condensate of SAR abolisher according to a sixth aspect, carbon, platinum, platinum salt, gold, vanadium, or palladium is used as the hydrogen adsorbent cited in the fifth aspect.

In the method of producing condensate of SAR abolisher according to a seventh aspect, NaCl or NaOH is used as the electrolyte cited in the fifth aspect.

The condensate of SAR abolisher according to an eighth aspect is produced by reducing a solution containing electrolyte and hydrogen adsorbent by electrolysis, and by condensing the obtained electrolytic reduced water.

The powder of SAR abolisher according to a ninth aspect is produced by reducing, by electrolysis, a solution of purified water with electrolyte and hydrogen adsorbent dissolved therein, and by evaporating the obtained electrolytic reduced water to dryness.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1 illustrates steps of producing condensate of SAR abolisher according to a first example of the present invention.

FIG. 2 is a diagram showing an electrolytic reduced water generator.

FIG. 3 illustrates an effect of the condensate of SAR abolisher.

FIG. 4 illustrates relation between degree of concentration of the condensate of SAR abolisher and OH. radical abolishing capability.

FIG. 5 is a diagram illustrating a method of producing condensate of SAR abolisher according to a second example of the present invention.

DESCRIPTION OF THE PREFERRED EMBODIMENTS

EXAMPLE 1

Figure 1:
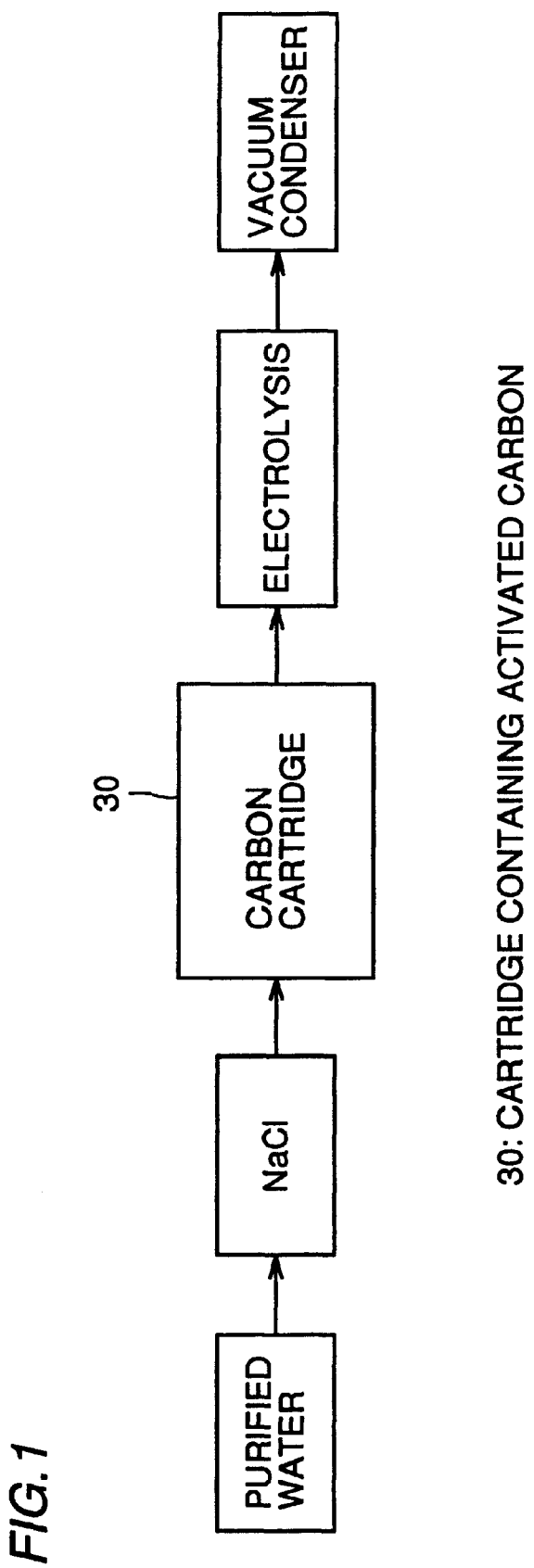

Steps of producing condensate of SAR abolisher according to the present invention will be described with reference to FIG. 1.

Electrolyte (0.01% NaCl and 0.008% NaOH) is introduced into super purified water (e.g., purified water passed through a reverse osmosis membrane). The solution of the purified water with the electrolyte dissolved therein is caused to pass through a cartridge 30 including hydrogen adsorbent (i.e., active carbon with its primary component being carbon).

The hydrogen adsorbent employed in the present example were those including fibrous active carbon, granulated active carbon with silver attached thereto (hereinafter, referred to as "silver-coated granulated active carbon"), and binder fiber, respectively, as shown in Table 1 below. Table 2 shows detailed data as to the performance or qualities of the fibrous active carbon (FR-20) and the silver-coated granulated active carbon (T-SB48/100).

TABLE 1

| Component | Name | Content (weight %) |
| --- | --- | --- |
| Fibrous active carbon | FR-20 | 46.5 |
| Silver-coated granulated active carbon | T-SB48/100 | 46.5 |
| Binder fiber | | 7.0 |

TABLE 2

| Performance etc. | Unit | FR-20 | T-SB48/100 |
| --- | --- | --- | --- |
| Adsorbable amount of iodine | mg/g | ≧1850 | ≧1400 |
| Adsorbable amount of benzene | weight % | ≧50 | ≧45 |
| Packed density | g/ml | — | 0.38–0.44 |
| Amount of attached silver | weight % | — | 0.08–0.14 |

Figure 2:
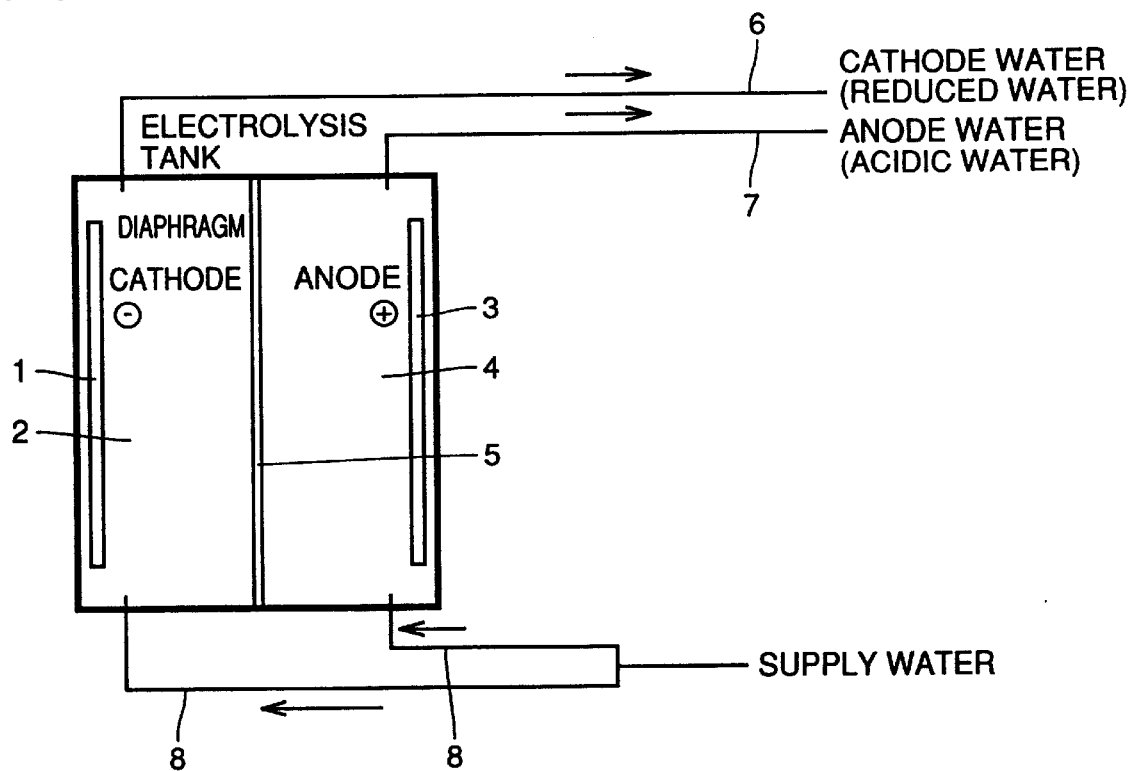

The solution passed through cartridge 30 is then electrolyzed in an electrolysis tank (TI-8000) as shown in FIG. 2.

The electrolysis was conducted under the following conditions. The above-described solution was introduced into both a cathode chamber 2 and an anode chamber 4. Between a cathode 1 and an anode 3, electricity was applied to electrolyze the solution, for at least 0.5 seconds but no longer than 5 seconds, in a room temperature (18° C.–22° C.). At this time, the amount of the current being applied was selected within a range from 0.16 mA/cm$^2$ to 3.2 mA/cm$^2$ per two electrodes and one diaphragm.

Electrolytic reduced water obtained in cathode chamber 2 is then condensed using a rotary evaporator (vacuum condenser) at 60° C. Thus, condensate of the electrolytic reduced water, i.e., condensate of SAR abolisher, is obtained.

Here, a small amount of white powder was obtained by completely removing water from the electrolytic reduced water using the rotary evaporator. This white powder is Na in NaOH that was added to the purified water as catalyst, or a mixture of Na and active carbon. It was found that the powder thus obtained also had potency to abolish SAR, as will be described later.

The generation of such mixture of Na and active carbon can be explained by considering that carbon was first dissolved into the purified water during its passing through cartridge 30; active hydrogen generated by electrolysis was adsorbed by the carbon; and the carbon having adsorbed the active hydrogen was precipitated.

In the present example, NaCl and NaOH have been used as the electrolyte. However, the present invention is not limited thereto. Any substance that can be ionized when dissolved into water may be used alternatively.

Further, in the present example, carbon dissolving into water during its passage through the cartridge has been used as the hydrogen adsorbent. However, the present invention is not limited thereto. Any substance that can adsorb hydrogen (H., H$_2$), such as platinum (Pt), platinum salt (H$_2$PtCl$_6$), gold (Au), vanadium (V), and palladium (Pd), may be used alternatively. In particular, platinum (Pt), gold (Au), vanadium (V) and palladium (Pd), each of no more than 50 mesh, preferably of a diameter of 350 μm to 300 μm, are preferred.

Figure 3:
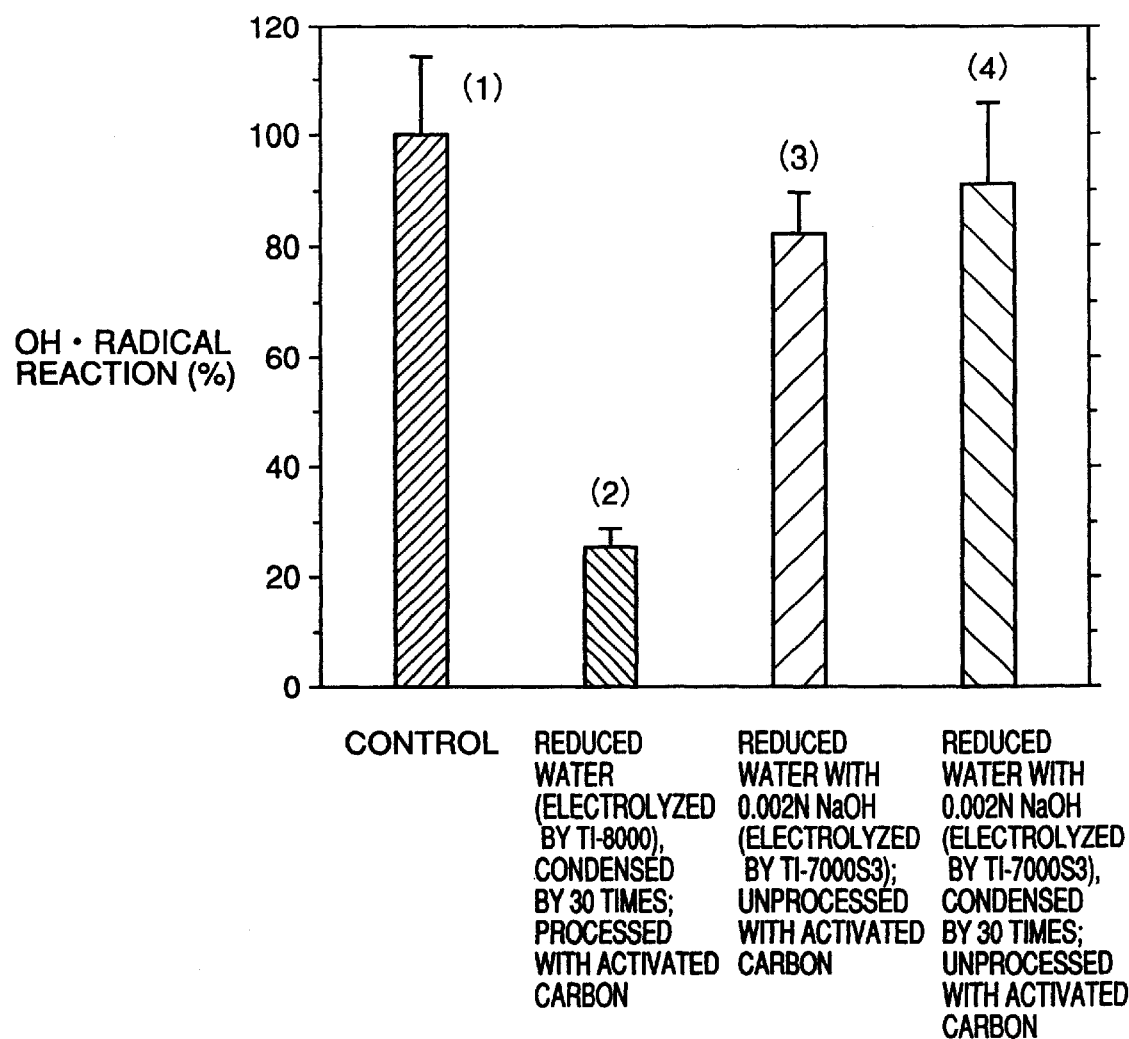

FIG. 3 illustrates comparison of OH. radical abolishing capabilities of the electrolytic reduced water processed with active carbon as described above and the electrolytic reduced water unprocessed with active carbon. OH. radical is equivalent to SAR, which was generated by Fenton reaction (H$_2$O$_2$+Fe$^{2+}$) as below, and detected by luminescent reagent luminol.

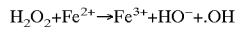

$$H_2O_2 + Fe^{2+} \rightarrow Fe^{3+} + HO^- + .OH$$

Detailed procedures are as follows. First, a solution having the following composition was prepared:

Reduced water (obtained with the conditions stated above) 440 μl

1M Tris hydrochloric acid buffer solution (pH: 7.8) 10 μl 0.01 mM Hydrogen peroxide 20 μl 0.1 mM FeSO$_4$+DETAPAC (1 mM) 20 μl Total 500 μl Next, an intensity of chemiluminescence of luminol by OH. radical was measured using a CLA instrument (CLD-110 type) available from Tohoku Denshi Kogyo Co. A relative luminescence intensity was then calculated, with a luminescence intensity obtained when using super purified water instead of the reduced water being represented as 100%. Thus, SAR abolishing capabilities of various kinds of reduced water were examined. FIG. 3 shows the results.

Referring to FIG. 3, (1) represents the result obtained when unprocessed purified water was used. (2) represents the result obtained in the case where a solution of super purified water with 0.01% NaCl dissolved therein was processed with active carbon as described above, electrolyzed using TI-8000, and the electrolytic reduced water obtained was condensed by 30 times. Herein, the term "condensed by 30 times", for example, means that water is reduced in volume by a factor of 30, or more specifically, 300 cc of electrolytic reduced water is condensed to the volume of 10 cc.

In FIG. 3, (3) represents the result obtained in the case where a solution of super purified water with 0.002N of NaOH as the electrolyte added therein, unprocessed with active carbon, was electrolyzed using an electrolysis apparatus TI-7000S3 (a strong electrolysis apparatus formed of three TI-8000 connected in series) having greater electrolytic capability than TI-8000. (4) represents the result obtained in the case where the sample obtained at (3) was condensed by 30 times.

Figure 4:
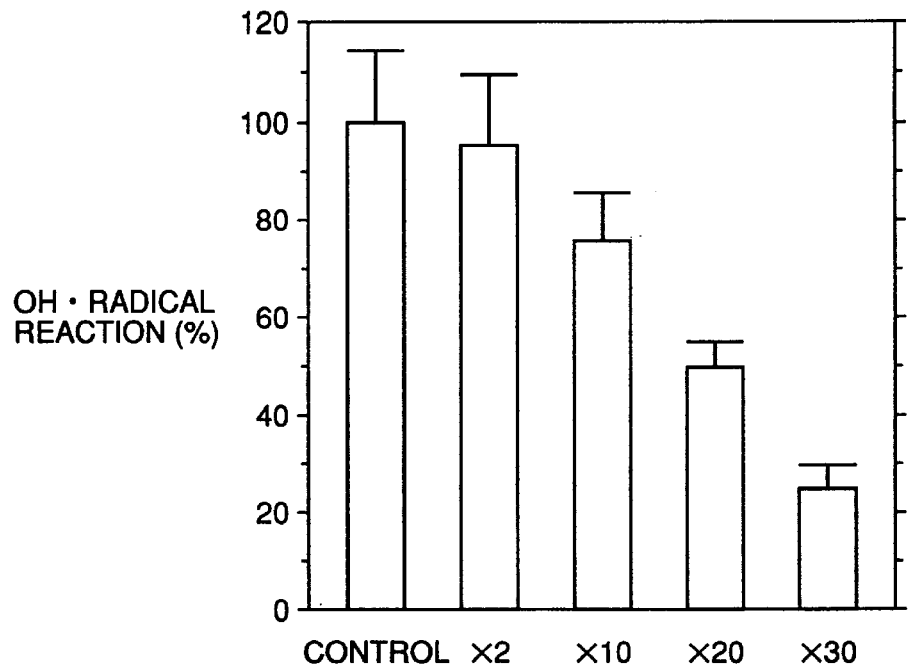
Figure 5:
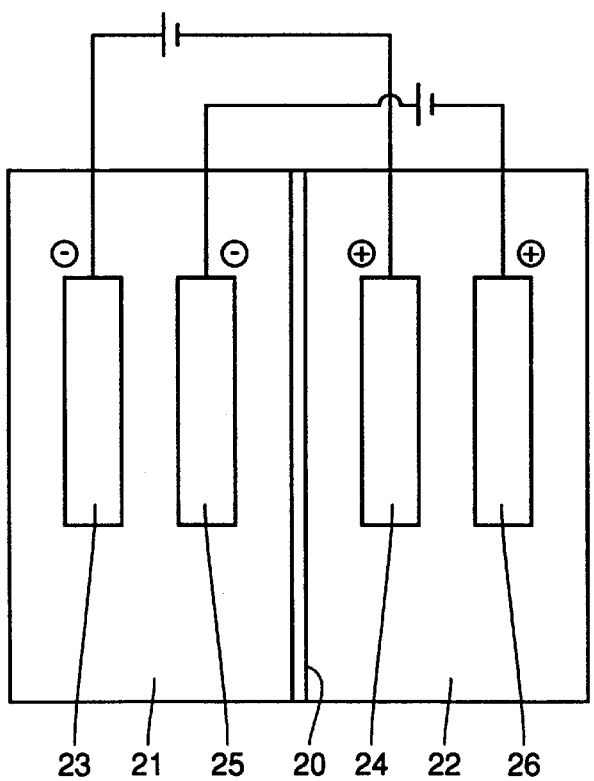

FIG. 4 shows comparison of OH. radical abolishing capabilities of the electrolytic reduced waters processed with active carbon, condensed in different degrees. In FIGS. 3 and 4, CONTROL represents the value obtained when super purified water was used for testing.

Table 3 lists numerical data corresponding to the results shown in FIG. 4.

TABLE 3

| | OH · radical reaction (%) |
|---|---|
| CONTROL | 100 |
| × 2 | 96 |
| × 10 | 74 |
| × 20 | 48 |
| × 30 | 23 |

× 2: reduced water condensed by 2 times
× 10: reduced water condensed by 10 times
× 20: reduced water condensed by 20 times
× 30: reduced water condensed by 30 times Referring to FIGS. 3 and 4 and Table 3, it was found that the OH. radical reaction decreased by condensing the electrolytic reduced water processed with active carbon.

Thus, condensate of SAR abolisher exhibiting strong and stable SAR abolishing capability was obtained by causing a solution of super purified water with 0.01% NaCl dissolved therein to pass through an active carbon filter containing carbon (C) as hydrogen adsorbent before electrolysis by TI-8000, and by condensing the obtained electrolytic reduced water.

Referring to (2) of FIG. 3, when the electrolyte-containing solution, processed with active carbon, was electrolyzed using TI-8000, electrolytic reduced water exhibiting pH of 11.4 and oxidation-reduction potential (ORP) of −900 mV was obtained. It was proved that condensate of SAR abolisher having satisfactory SAR abolishing capability was obtained by condensing this water.

Referring to (3) of FIG. 3, when the solution of super purified water with 0.002N (0.008%) of NaOH added therein was electrolyzed using strong electrolysis apparatus TI-7000S3 formed of a series of three TI-8000, the electrolytic reduced water exhibiting SAR abolishing capability to some extent was obtained. This means that it is basically possible to generate active hydrogen even if the water is not passed through active carbon. However, the SAR abolishing capability is increased when the water is processed with active carbon, which is considered because the carbon adsorbs active hydrogen, thereby stabilizing the same.

Further, a solution obtained by adding 0.01% NaCl to super purified water was passed through a filter of active carbon and electrolyzed. Electrolytic reduced water thus obtained was evaporated to dryness using a rotary evaporator at a temperature of 60° C. Solid material thus obtained was then dissolved into the super purified water. When the water was condensed by twice, the SAR abolishing capability doubled approximately. When the water was condensed by ½, the capability approximately halved. Thus, it was revealed that the active hydrogen could be condensed.

The electrolytic reduced water condensed by 30 times exhibited strong SAR abolishing activity, or, activity to strongly abolish most dangerous OH. radical. It also exhibited capabilities to abolish strong active oxygen ($O_2^-$.) and $H_2O_2$.

Referring to (4) of FIG. 3, when the super reduced water containing 0.002N (0.008%) of NaOH was condensed by 30 times, it did not exhibit strong OH. radical abolishing capability. It was determined that the active hydrogen was not condensed in this case. This is considered because any substance that is capable of stabilizing the active hydrogen is not dissolved in this electrolytic reduced water.

Referring to Table 3, the level of the SAR abolishing reaction changed according to the degree of concentration of the electrolytic reduced water. Thus, it was found that the active hydrogen within the electrolytic reduced water reacts according to the law of amount and function.

EXAMPLE 2

FIG. 5 illustrates a method of producing condensate of SAR abolisher according to the second example. A solution obtained by dissolving NaOH, NaCl or the like into purified water is introduced into a cathode chamber 21 and an anode chamber 22 separated from each other by a diaphragm 20. A first cathode 23 for electrolysis is immersed in cathode chamber 21, and a first anode 24 for electrolysis is immersed in anode chamber 22.

A second cathode 25 is also immersed in cathode chamber 21, and a second anode 26 formed of hydrogen adsorbent (C, Pt, $H_2PtCl_6$, Au, V or Pd) is immersed in anode chamber 22 for application of electricity between itself and second cathode 25. Electricity is applied between first cathode 23 and first anode 24 to electrolyze the solution. Electricity is also applied between second cathode 25 and second anode 26 to cause the hydrogen adsorbent to dissolve into the solution. Thereafter, the electrolytic reduced water produced within cathode chamber 21 is derived, and water contained in the derived electrolytic reduced water is evaporated using a rotary evaporator.

With such a method, again, condensate of SAR abolisher exhibiting strong and stable SAR abolishing activity was obtained. This is considered because the hydrogen adsorbent of second anode 26 was dissolved into the solution and transferred via diaphragm 20 to cathode chamber 21, where it adsorbed the active hydrogen (H.), so that the active hydrogen was stabilized and condensed.

The quantitative analysis of the active hydrogen was performed as follows.

$WO_3$ (yellow) turns blue when it specifically adsorbs the active hydrogen. $WO_3$ does not adsorb hydrogen molecules. Utilizing such reaction, it is possible to detect the active hydrogen by discoloration of $WO_3$.

The detailed procedures were as follows.

12.6 mg of $WO_3$ was added to 500 ml of reduced water. It was cooled with iced water for 30 minutes, and then stirred. The solution thus obtained was subjected to centrifugation, supernatant was discarded, and $WO_3$ precipitated at the bottom was recovered. Thus recovered $WO_3$ was placed in a 96-well micro plate, which was stirred by a voltec mixer, subjected to centrifugation, and $WO_3$ was collected at the bottom layer of the well. An image of colored $WO_3$ was captured by an image scanner into a personal computer. Using an image processing software (PhotoShop), the degree of coloration of $WO_3$ was quantified. Thereafter, it was compared with a degree of coloration as the reference that would be obtained when using super purified water. Thus, a relative amount of the active hydrogen being contained was determined.

According to the present example, the amount of the hydrogen adsorbent to be dissolved from second anode 26 can be controlled by altering the magnitude of the current flowing between second cathode 25 and second anode 26. Correspondingly, it is also possible to control the amount of active hydrogen (H.) to be adsorbed.

In the present invention, it has become clear that active hydrogen within electrolytic reduced water can be condensed by causing a solution of purified water with electrolyte dissolved therein to be processed with active carbon before being electrolyzed. Such condensed active hydrogen exhibiting strong SAR abolishing capability may be applicable to prevention and treatment of many diseases listed as follows, including cancer, diabetes, arteriosclerosis, allergic reaction, Parkinson's disease, and Alzheimer's disease, for which excessive SAR and lipid peroxide are named as their causes or exacerbating factors.

The diseases said to be caused by such excessive SAR or lipid peroxide include: cerebral stroke (cerebral hemorrhage, cerebral infarction, cerebral thrombosis), cardiac infarction, arteriosclerosis, cancer, thrombopathy, high-degree lipemia, diabetes, hepatitis, nephritis, ulcer, gastric mucosa disorder, pneumonia, cataract, retinitis pigmentosa, retinodialysis, autoimmune diseases such as collagen diseases, articular rheumatism, AIDS, Parkinson's disease, Alzheimer's disease, encephalopathy, lung scleroma, allergic diseases such as atopic dermatitis, gout, blotches, freckles, wrinkles, dermatitis, neuralgia, hypertension, prostatomegaly, gastroenteropathy, arrhythmia, epilepsy, rough dry skin, aging, menopausal syndrome, Meniere's disease, wart, hangover, fatigue, pollinosis, cold, depression, trigeminal neuralgia, cholelithiasis, nasal polyp, chronic diarrhea, constipation, hives, backache, excessive cholesterol, disorder of pregnancy, decline of virility, obesity, menstrual irregularity, asthma, acne, eczema, summer blahs, autonomic imbalance, and others. Further, the present invention is expected to improve enterobacterium flora by bacteriostasis.

Moreover, the present invention can also be used for plants that are constantly exposed to strong stresses due to oxidation. The present invention is expected to make the plants resistant to insects causing damage, and tolerant to dryness, continual rain, and sequential cropping. In addition, it is expected to promote growth and increase harvest of fruits, and also promote growth of roots. In fact, it has become clear that the condensate of electrolytic reduced water obtained by the present invention, i.e., the condensate and powder of SAR abolisher, has the following advantages.

1. It suppresses growth of cancer cells.
2. It suppresses colony formation of the cancer cells within soft agar culture.
3. It changes conformation of the cancer cells.
4. It reduces activity of telomere specific binding protein of the cancer cells, and shortens the telomere length dependent on the number of times of cell division.
5. It prevents intranuclear localization of telamelaze.
6. It suppresses metastasis of the cancer cells.
7. It suppresses growth of the cancer cells in the body of mouse.
8. It promotes sugar intake to muscle and lipocyte. It has become clear that the operation mechanism is based on the fact that it promotes transfer of sugar transporter GLUT-4 to cell membrane by activity of P1-3 kinase, as is the case of insulin.
9. When using together with platinum ion ($H_2PtCl_6$), it operates synergistically to alleviate sugar tolerance disorder of II type diabetes model mouse (db/db mouse).

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of producing condensate of superoxide anion radical (SAR) abolisher, comprising the steps of:

introducing hydrogen adsorbent into a solution obtained by dissolving electrolyte into purified water;

introducing said solution containing said hydrogen adsorbent into both a cathode chamber and an anode chamber separated from each other by a diaphragm;

with a cathode immersed in said cathode chamber and an anode immersed in said anode chamber, applying electricity between the cathode and the anode to electrolyze said solution;

deriving electrolytic reduced water from said cathode chamber; and evaporating water within said electrolytic reduced water.

2. The method of producing condensate of SAR abolisher according to claim 1, wherein said hydrogen adsorbent includes one of carbon, platinum, platinum salt, gold, vanadium and palladium.

3. The method of producing condensate of SAR abolisher according to claim 1, wherein said electrolyte includes one of NaCl and NaOH.

4. The method of producing condensate of SAR abolisher according to claim 1, wherein said step of introducing hydrogen adsorbent into a solution obtained by dissolving electrolyte into purified water includes the step of causing said solution containing electrolyte to pass through a cartridge including the hydrogen adsorbent.

5. A method of producing condensate of SAR abolisher, comprising the steps of:

introducing a solution obtained by dissolving electrolyte into purified water into both a cathode chamber and an anode chamber separated from each other by a diaphragm;

immersing a first cathode for electrolysis in said cathode chamber and immersing a first anode for electrolysis in said anode chamber;

immersing a second cathode in said cathode chamber and immersing a second anode formed of hydrogen adsorbent in said anode chamber for application of electricity between the second anode and said second cathode;

applying electricity between said first cathode and said first anode to electrolyze said solution;

applying electricity between said second cathode and said second anode to dissolve said hydrogen adsorbent into said solution;

deriving electrolytic reduced water produced within said cathode chamber; and evaporating water within said electrolytic reduced water.

6. The method of producing condensate of SAR abolisher according to claim 5, wherein said hydrogen adsorbent includes one of carbon, platinum, platinum salt, gold, vanadium and palladium.

7. The method of producing condensate of SAR abolisher according to claim 5, wherein said electrolyte includes one of NaCl and NaOH.

8. Condensate of SAR abolisher obtained by reducing a solution containing electrolyte and hydrogen adsorbent by electrolysis, and by condensing electrolytic reduced water obtained.

9. Powder of SAR abolisher obtained by reducing, by electrolysis, a solution containing electrolyte and hydrogen adsorbent, and by evaporating obtained electrolytic reduced water to dryness.

* * * * *